(12) United States Patent
Liu et al.

(10) Patent No.: US 6,271,038 B1
(45) Date of Patent: Aug. 7, 2001

(54) METHODS FOR HIGH THROUGHOUT DETERMINATION AND RANKING OF FORMULATIONS AND SOLUBILITY

(75) Inventors: Xiaoli Liu, Mountain View; Lori H. Takahashi, San Jose, both of CA (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/461,258

(22) Filed: Dec. 15, 1999

(51) Int. Cl.$^7$ .................................................... G01N 30/00
(52) U.S. Cl. .......................... 436/161; 436/180; 204/450; 204/451
(58) Field of Search .................................. 204/450, 451, 204/600, 601; 436/161, 180; 422/70, 100

(56) References Cited

U.S. PATENT DOCUMENTS

| | | | |
|---|---|---|---|
| 5,785,831 | * | 7/1998 | Bek ........................................ 204/451 |
| 5,797,898 | | 8/1998 | Santini, Jr. et al. . |
| 5,800,690 | | 9/1998 | Chow et al. . |
| 5,842,787 | | 12/1998 | Kopf-Sill et al. . |
| 5,858,195 | * | 1/1999 | Ramsey .................................. 204/601 |
| 5,869,004 | | 2/1999 | Parce et al. . |
| 5,876,675 | | 3/1999 | Kennedy . |
| 5,882,465 | | 3/1999 | McReynolds . |
| 5,885,470 | | 3/1999 | Parce et al. . |
| 5,942,093 | * | 8/1999 | Rakestraw et al. ................... 204/450 |
| 5,942,443 | | 8/1999 | Parce et al. . |
| 5,955,028 | | 9/1999 | Chow . |
| 5,957,579 | | 9/1999 | Kopf-Sill et al. . |
| 5,958,694 | | 9/1999 | Nikiforov . |
| 5,964,995 | | 10/1999 | Nikiforov et al. . |
| 5,965,001 | | 10/1999 | Chow et al. . |
| 5,965,410 | * | 10/1999 | Chow et al. .......................... 435/91.2 |
| 5,984,227 | | 11/1999 | Yamaguchi et al. . |
| 6,068,767 | * | 5/2000 | Garguilo et al. ................... 210/198.2 |
| 6,150,180 | * | 11/2000 | Parce et al. ........................... 436/514 |
| 6,153,073 | * | 11/2000 | Dubrow et al. ...................... 204/453 |
| 9,956,410 | | 9/1999 | Brisson . |

FOREIGN PATENT DOCUMENTS

WO 98/00231   1/1998   (WO) .............................. B01J/19/00

OTHER PUBLICATIONS

Jacobson, S.C. "Open Channel Electrochromatography on a Microchip" Analytica Chemistry, vol. 66, No. 14, Jul. 15, 1994, pp. 2369–2373.*

(Sep. 1, 1999), "Minaturized mixture," Analytical Chemistry News & Features.

S. Borman (Feb. 1, 1999), "Microchips delivery on command," C&EN, pp. 30–31.

List of companies making or developing CEC/CE microchips, date unknown.

(Aug. 19, 1999), CEC '99, 3$^{rd}$ International Symposium on Capillary Electrochromatography, Workshop Lecture Summaries.

John H. Miyawa et al. (1998), "Capillary electrochromatography as a method development tool for the liquid chromatographic separation of DUP 654 and related substances," Journal of High Resolution Chromatography, 21(3):161–168.

Michael Freemantle (Feb. 22, 1999), "Downsizing Chemistry," C&EN, pp. 27–36.

* cited by examiner

Primary Examiner—Jeffrey Snay
(74) Attorney, Agent, or Firm—Townsend and Townsend and Crew, LLP

(57) ABSTRACT

The invention provides apparatus and methods for formulation mixing and measurement to produce rank orders of solubility of chemicals in a variety of formulations. One such method includes mixing a volume of a stock solution having a known concentration of a chemical with a volume of a base liquid to form a control sample. Another volume of the stock solution is mixed with a volume of a formulation to form a test sample. The control sample is passed through a capillary electrochromatography (CEC) tube to separate the chemical from the base liquid, and the test sample is passed through a CEC tube to separate the chemical from the formulation. The method includes measuring the amount of chemical passing through the CEC tubes for both the control sample and the test sample, and comparing the measured amount of chemical from the control sample with the measured amount of chemical from the test sample to determine the solubility of the chemical in the formulation relative to the base liquid.

17 Claims, 4 Drawing Sheets

METHODS FOR HIGH THROUGHOUT DETERMINATION AND RANKING OF FORMULATIONS AND SOLUBILITY

BACKGROUND OF THE INVENTION

The present invention relates generally to apparatus and methods for formulation and solubility testing and ranking, and more specifically to apparatus and methods of using electro-osmotically driven systems for formulation mixing and measurement to produce rank orders of solubility for a variety of formulations and test media.

High throughput synthesis and screening are producing large numbers of potent and selective compounds, but more and more highly lipophilic compounds are emerging from these lead discovery initiatives. Many new lead compounds are relatively insoluble in water, which presents challenges in developing formulations for both oral and intravenous (TV) administration.

Choosing the right formulation can enhance the solubility of these poorly soluble drugs, improve the stability of unstable drugs, assist in controlling and sustaining the delivery of a particular drug, aid in targeted deliver, and minimize the pain during injection or minimize unwanted side effects. In a traditional drug development setting, formulation or test media development is a labor and time intensive task usually performed with several milligrams of compound.

Once compounds have been selected for development, formulating typically consists of dissolving compounds in water-miscible cosolvents—e.g., propylene glycol, polyethylene glycol, glycerin, ethanol, etc. Other methods of formulating water-insoluble drugs involve the use of solubilizing agents, detergents or altering the pH of the solutions. New formulation approaches include the use of emulsions, liposomes, nanospheres, and cyclodextrins (CDs).

The typical procedure for determining suitable formulations involves "dissolving" the compound into various formulations and using conventional analytical methodology for determining maximum concentrations. Analytical methods such as spectroscopic methods (UV-Vis) and high performance liquid chromatography (HPLC) are often used as well as visual examinations. Visual or spectroscopic methods require larger amounts of material.

The large number of lead compounds arising from combinatorial efforts in addition to the small quantities being synthesized have created a need for higher throughput formulating using small amounts of material. Formulating for in vivo testing using micrograms of material is quickly becoming a bottleneck for rapid assessment of a combinatorial chemistry drug's phannacokinetic profile and efficacy. Further, many of the compounds arising from combinatorial libraries are uncharged and highly lipophilic in nature and prevent the use of capillary zonal electrophoresis (CZE).

Hence, the invention is related to apparatus and methods which permit small amounts of material to be rapidly analyzed for solubility in a variety of test media, many of which are potential formulations.

SUMMARY OF THE INVENTION

The present invention provides apparatus and methods for formulation and solubility testing and ranking. More specifically, apparatus and methods of the present invention may use electro-osmotically driven systems for formulation mixing, or off-line mixing, and measurement to produce rank orders of compound solubility in a variety of test media and formulations.

In one embodiment, the present invention provides a method for evaluating the solubility of a chemical in a formulation or test medium. The method includes mixing a volume of a stock solution that has a known concentration of a chemical with a volume of a base liquid to form a control sample. Another volume of the stock solution is mixed with a volume of a formulation to form a test sample. The control sample is passed through a capillary electro-chromatography (CEC) tube (where tube refers to a bed or channel) to separate the chemical from the base liquid, and the test sample is passed through a CEC tube to separate the chemical from the formulation. The method includes measuring the amount of chemical passing through the CEC tubes for both the control sample and the test sample, and comparing the measured amount of chemical from the control sample with the measured amount of chemical from the test sample to determine the solubility of the chemical in the formulation relative to the base liquid. In this manner, use of the CEC tube facilitates the rapid determination of a chemical's solubility in a particular formulation. In one aspect, the concentration of the chemical in the formation is calculated based on the comparison and the known concentration of the stock solution.

In one aspect, the method includes mixing known volumes of the stock solution with volumes of other formulations to form multiple test samples. The test samples are passed through CEC tubes, and the amount of chemical passing through each CEC tube is measured. The method includes ranking the test samples based on a comparison of the amount of chemical measured for each test sample with the amount of chemical measured from the control sample. In this manner, rank ordering of a chemical's solubility in a large number of different formulations or test media is rapidly achieved.

In some aspects, the stock solution and/or the base liquid comprises dimethyl sulfoxide (DMSO). In another aspect, the chemical is hydrophobic. In other aspects, the chemical is uncharged and/or lipophilic. In one aspect, the volume of the base liquid is generally equal to the volume of the formulation to facilitate comparisons of chemical concentrations therein.

The measuring step may be accomplished in a number of ways. For example, the chemicals may be measured by counting ions with a mass spectrometer, by measuring a fluorescent signal emitted from the chemical, by measuring the amount of light absorption or reflection by the chemical, and the like.

In one aspect, the method includes moving the control sample and the test sample(s) through channels formed in a substrate using electrical potentials to supply the control sample and the test sample to the CEC tubes. Similarly, in another aspect the mixing steps include moving the stock solution, the base liquid and the formulation through mixing channels in a substrate using electrical potentials.

In another embodiment of the invention, a method for ranking the solubility of a chemical in a plurality of formulations includes providing a substrate having multiple wells and fluid delivery channels, including a stock solution well and formulation wells. A volume of a stock solution having a known concentration of a chemical is placed into the stock solution well. A base liquid and different formulations are placed into the formulation wells. The method includes applying an electrical potential to mix a volume of the stock solution from the stock solution well with a volume of the base liquid from one of the formulation wells to form a control sample; applying electrical potentials to mix other volumes of the stock solution from the stock solution wells with volumes of the formulations from the formulation wells to form multiple test samples; and applying electrical potentials to move the control sample and the test samples through at least some of the fluid channels and into and through CEC tubes. The amount of chemical passing through the CEC tubes is measured for the control sample and the test samples. The method further includes comparing the measured amount of chemical from the control sample with the measured amount of chemical from each of the test samples to determine the solubility of the chemical in the formulations relative to the base liquid.

In one aspect, an electrical potential is applied for a desired period of time to move the volumes of stock solution, base liquid and formulations from their respective wells and into the fluid delivery channels. In another aspect, the control and test samples are mixed by alternating the electrical potential polarity a sufficient number of times to mix the volumes of stock solution and base liquid, and to mix the volumes of stock solution and formulations, respectively.

The invention further includes exemplary devices for practicing methods of the invention. In one embodiment, a liquid processing device of the invention includes a substrate having multiple fluid channels, and a plurality of CEC tubes operably coupled to the substrate so as to each be in fluid communication with one of the channels. The device has a set of electrodes that are adapted to move solutions through the channels and the CEC tubes when an electrical potential is applied between the electrodes.

In one aspect, the substrate includes wells in fluid communication with the channels. Preferably, the electrodes are disposed in the wells. In another aspect, the substrate includes a mixing channel disposed between at least one of the wells and one of the CEC tubes. In one aspect, the CEC tubes comprise channels, such as silicon channels, that contain a stationary phase, such as $C_{18}$, although other stationary phases may be used within the scope of the present invention.

The invention further provides exemplary liquid processing systems. In one embodiment, the liquid processing system includes a substrate as previously described, with a detector coupled to the substrate and adapted to measure the solutions.

The detector may comprises a wide range of detectors within the scope of the invention, including a UV-Vis spectrophotometer (including diode array), fluorescence, nephelometric and mass spectrometric detectors, and the like.

In one embodiment, the liquid processing system further includes a controller coupled to the set of electrodes. In this manner, the voltage applied to the electrodes, and the duration and polarity thereof, may be controlled. In one embodiment, a plurality of detectors are included, with each detector coupled to one of the CEC tubes.

In one aspect, solutions moved through the system comprise a mixture of a chemical-containing stock solution with a formulation or a base liquid. Preferably, the detector is adapted to measure a solubility of the chemical in the formulations compared to a solubility of the chemical in the base liquid.

These and other embodiments of the present invention along with many of its advantages and features are described in more detail in conjunction with the text below and attached figures.

DESCRIPTION OF THE SPECIFIC EMBODIMENTS

Figure 1:
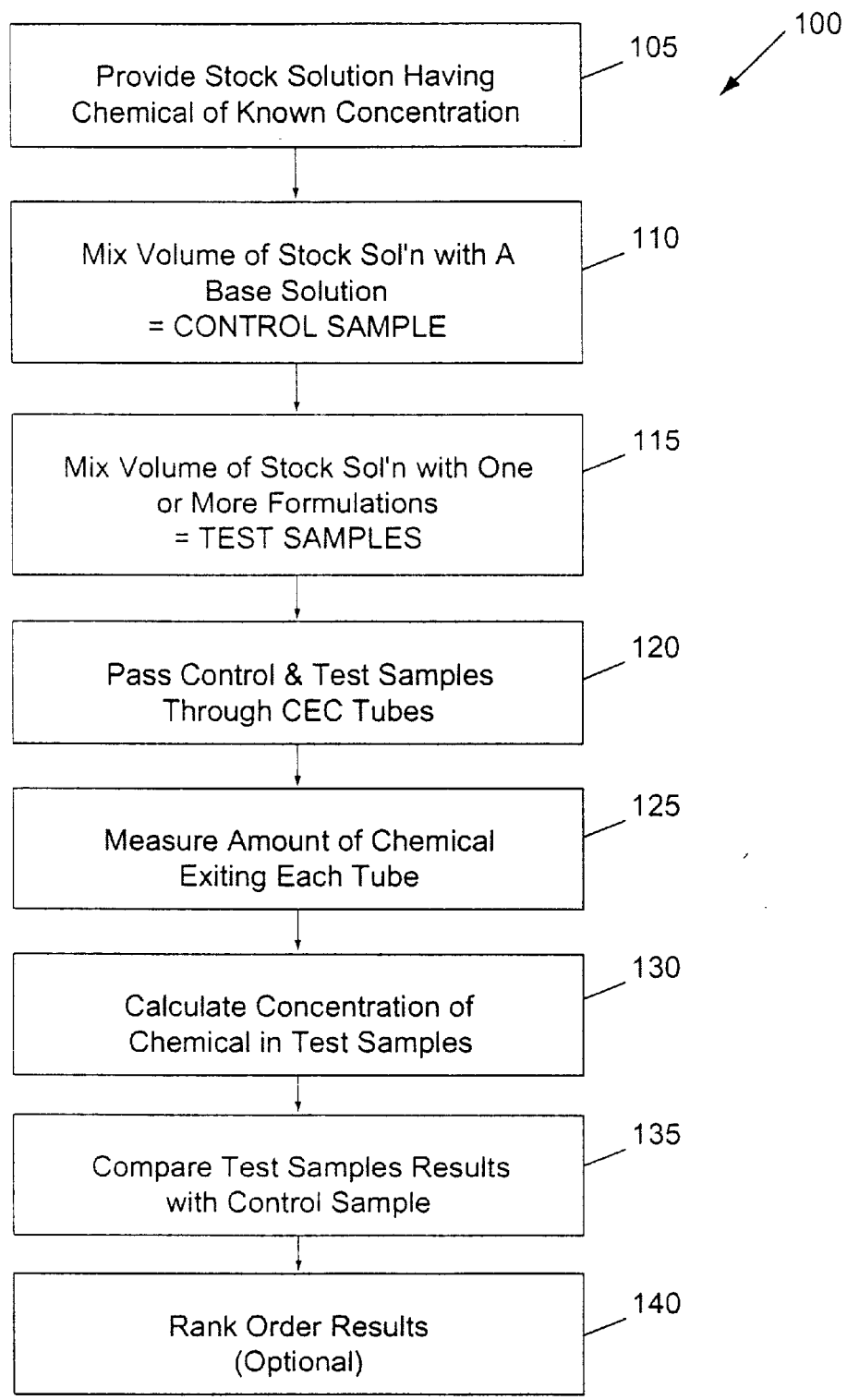
FIG. 1 depicts a flowchart illustrating one exemplary method of ranking chemical solubility according to the present invention.

The invention uses capillary electrochromatography (CEC) systems to mix and transport formulations in a rapid manner. Capillary electrochromatography combines the advantages of capillary zonal electrophoresis (CZE) and micro-HPLC.

The CZE technique, in which a voltage potential is applied to a buffer-filled capillary to generate electro-osmotic flow, provides excellent efficiency in separating charged species via their different electrophoretic mobilities. In CZE, the capillary is typically made of silica, a material that forms fixed negative charges on the inner capillary wall in the presence of a solution of the correct pH containing electrolytes. Before the voltage gradient is applied, cations in the electrolyte solution will be attracted to these fixed negative charges, forming a so-called double layer at the capillary wall. Application of the voltage gradient creates a net movement of the cations loosely associated with the fixed negative charges at the electrolyte-silica interface. This movement, referred to as electro-osmotic flow, causes the bulk of the electrolyte solution to be dragged toward the negatively charged discharge outlet. A key disadvantage of the CZE approach, however, is that it cannot be used to resolve neutral-charged compounds.

Micro-BPLC, on the other hand, employs a stationary phase material in a capillary column and provides high selectivity in a wide range of applications because of the variety of stationary phase materials available for HPLC. The column efficiency, however, is reduced in micro-HPLC because the mobile phase is driven through the capillary separation column using high mechanical pump pressure, which results in a parabolic flow velocity profile.

CEC combines the high selectivity of micro-HPLC and the high efficiency of CZE. In CEC, the stationary phase can either be particles which are packed into the capillary tubes (packed CEC), or they can be attached (i.e., modified or coated) onto the walls of the capillary (open tubular or OTEC). The stationary phase material is similar to that used in micro-HPLC. The mobile phase, however, is pumped through the capillary column using an applied electric field to create an electro-osmotic flow, similar to that in CZE, rather than using high pressure mechanical pumps. This results in flat flow profiles which provide high separation efficiencies. The CEC approach can thus achieve the high efficiency of CZE. In addition, as in the case with micro-HPLC, CEC may be used to analyze neutral compounds that are not separable by CZE. This feature is useful since a number of compounds of interest developed by combinatorial chemistry are uncharged.

The miniaturization of the separation column by using a capillary column in CEC offers several advantages, including improved efficiency, mass detection sensitivity, low solvent consumption, small sample quantity, and easier coupling to a detectors such as mass spectrometers. Again, such advantages are helpful analyzing chemical compounds developed by combinatorial chemistry, since such compounds often are produced in small quantities. Further, the comparatively short process times available with CEC permit a large number of formulations to be examined. One additional advantage in the use of CEC is the ability to further miniaturize and multiplex the separations onto a chip-based format.

Turning now to FIG. 1, an exemplary method 100 for evaluating the solubility of a chemical in a formulation using CEC will be described. Method 100 includes providing a stock solution having a chemical of known concentration (Step 105). In one embodiment, the stock solution comprises dimethyl sulfoxide (DMSO), although other stock solutions may be used within the scope of the present invention. In one embodiment, the chemicals or selective compounds used, such as drug compounds, are those for which both oral and IV administration is desired. The chemical preferably is 100 percent dissolved in the stock solution.

The method includes mixing a volume of stock solution with a base liquid or solution to produce a control sample (Step 110). In one embodiment, the base solution also comprises DMS0. In this manner, the chemical remains fully dissolved, with the concentration diluted by the amount of the added base liquid. The method includes mixing a volume of stock solution, having the chemical to be tested, with one or more formulations to produce one or more test samples (Step 115).

The control and test samples are then passed through CEC tubes (Step 120). The CEC tubes operate to separate the chemical from the formulation or the base liquid. The method includes measuring the amount of chemical exiting each CEC tube (Step 125), calculating the concentration of the chemical in each test sample (Step 130), and comparing the results to that of the control sample (Step 135). The method further optionally includes producing a rank ordering of the results (Step 140). In this manner, CEC technology is used to analyze the solubility of a chemical in a number of potential formulations.

The comparing step may include, for example, comparing the peak areas for each test sample with the peak area for the control sample, as calculated by, for example, UV-Vis spectrophotometry. For embodiments using a chemical that is fully dissolved in a DMSO stock solution, the chemical is diluted by, but remains fully dissolved, when a DMSO base liquid is added. For each test sample, the measuring step can determine the amount of chemical that is dissolved in the formulation after passing through the CEC tube, and compare that amount to the amount of chemical that remains dissolved in the control sample. A comparative solubility value is then established for each test sample. A rank ordering then may be computed based on the chemical solubility in a number of different formulations as a function of control sample solubility.

Figure 2:
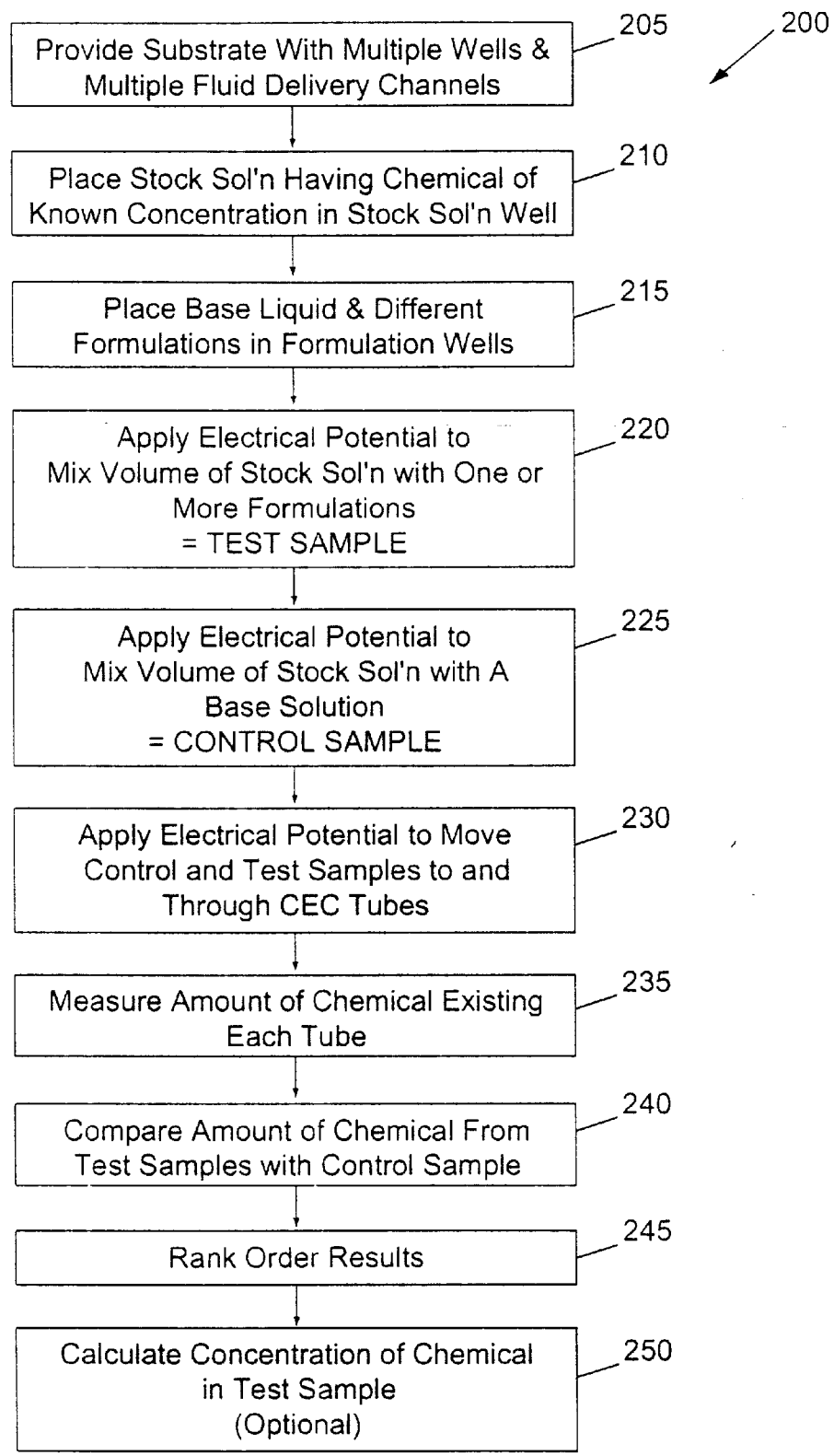
FIG. 2 depicts a flowchart illustrating another exemplary method of ranking chemical solubility according to the present invention.

FIG. 2 depicts another exemplary method 200 for ranking the solubility of a chemical in a plurality of formulations. Method 200 includes providing a substrate with multiple wells and multiple fluid delivery channels (Step 205). A stock solution, such as DMSO, having a chemical of known concentration is placed in a stock solution well (Step 210). A base liquid, such as DMSO, and a number of formulations are placed in formulation wells (Step 215). An electrical potential is applied to mix a volume of stock solution with a volume of base solution to produce a control sample (Step 220). Similarly, an electrical potential is applied to mix a volume of stock solution with one or more test formulations to produce one or more test samples (Step 225). An electrical potential is then applied to move the control and test samples to and through CEC tubes (Step 230).

The amount of chemical passing through a detection window associated with each CEC tube is measured (Step 235), and the amount of chemical from the test samples are compared with the amount of chemical from the control sample (Step 240). A rank order of results is produced (Step 245) and, optionally, the concentration of the chemical remaining in the test sample is calculated (Step 250). In this manner, methods of the invention may be carried out on a chip or substrate having capillary electrochromatography tubes.

Advantages of the invention include the need for only a small amount of chemical dissolved in the stock solution for testing its solubility in a large number of formulations. Such an advantage is helpful considering the small amounts of chemicals generally created by combinatorial chemistry. Another advantage is the ability to perform solubility testing in comparatively short periods of time. For instance, a run time using a fast, liquid chromatographic (HPLC) separation can be on the order of 2–3 minutes. Using a miniaturized CEC tube, separation can be achieved in a matter of several seconds. The ability to multiplex these separations using multichannel CEC technology would increase the overall efficiency dramatically. Typical volumes needed for HPLC separations are on the order of 10 microliters. Typical volumes used in CEC separations are on the order of several nanoliters. Still another advantage is the ability to analyze the solubility of neutral or uncharged chemical compounds.

Figure 3A:
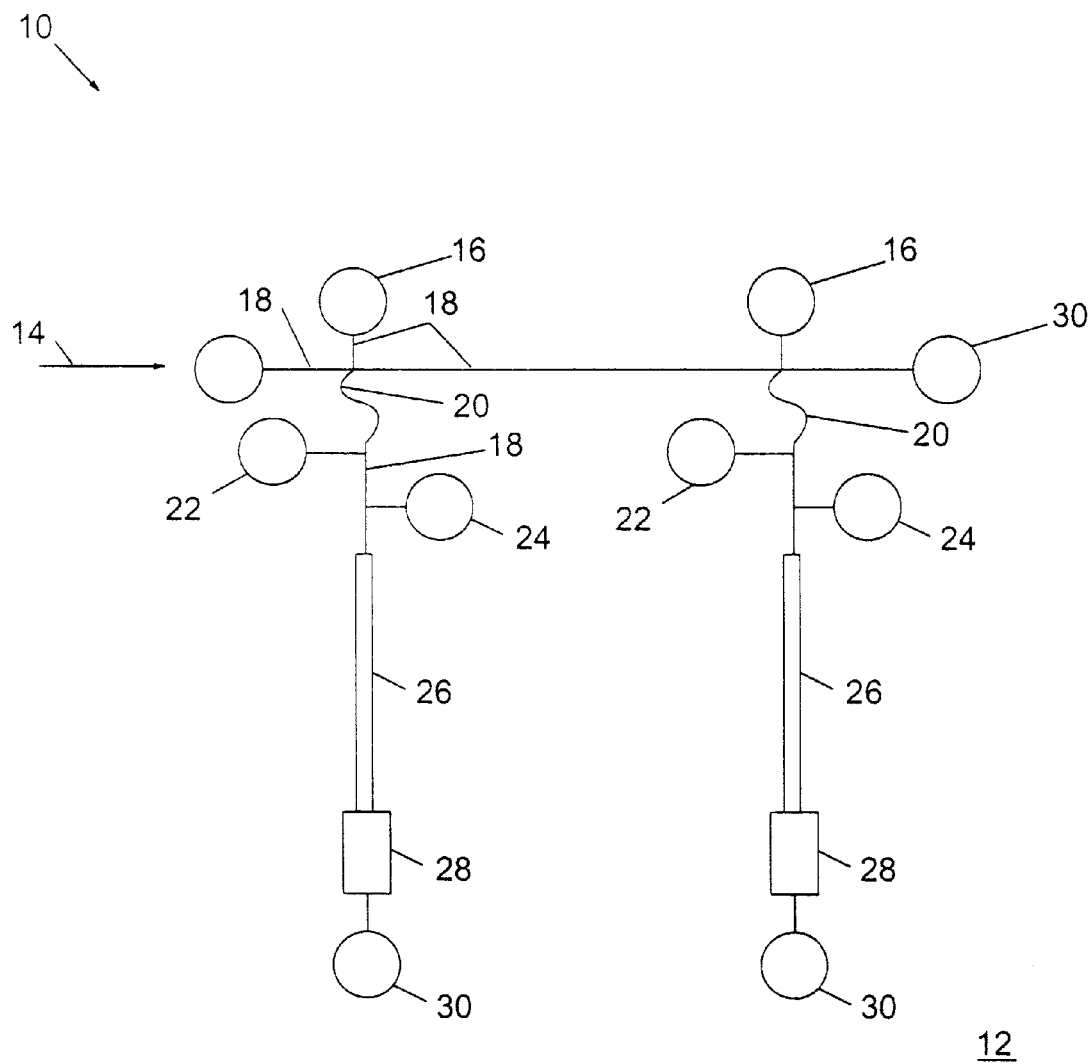
FIG. 3A illustrates a device for testing chemical solubility in a number of formulations according to the present invention.
Figure 3B:
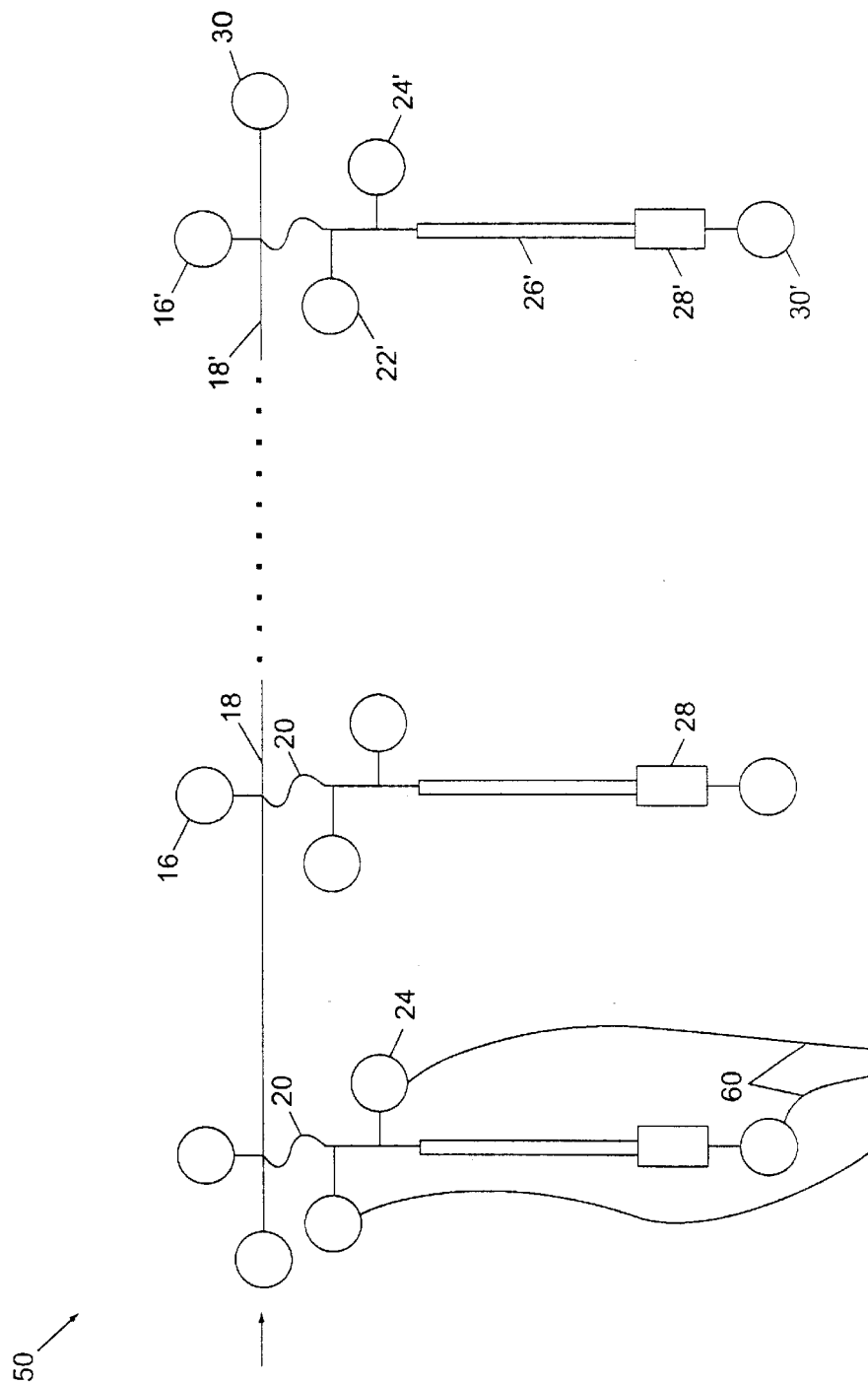
FIG. 3B depicts an exemplary liquid processing system of the present invention for testing and ranking chemical solubility.

Methods of the present invention may be carried out using devices and systems as depicted in FIGS. 3A and 3B. As shown in FIG. 3A, a device 10 of the present invention comprises a substrate 12 having a plurality of wells and fluid channels formed thereon.

Substrate 12 has a stock solution well 14 and a formulation well 16 fluidly coupled by a fluid channel 18. As the names imply, stock solution well 14 is used to introduce a stock solution into device 10, and formulation well 16 is used to introduce a formulation into device 10. The stock solution well 14 and formulation well 16 are coupled to a mixing coil 20 in which the two solutions are mixed. Mixing coil 20 may comprise, for example, a fluid channel having a nonlinear configuration. Another fluid channel 18 couples mixing coil 20 to CEC capillary tube 26. An injection well 22, a buffer well 24, and a waste well 30 also are fluidly coupled to CEC capillary 26.

Substrate 12 may comprise glass, quartz, ceramics, silicon and the like, as well as polymeric materials, e.g., plastics and the like. In the case of conductive or semiconductive substrates, there may be an insulating layer on the substrate. This permits the use of electro-osmotic forces to move materials through device 10. In the case of polymeric substrates, the substrate materials may be rigid, semi-rigid, or non-rigid, opaque, semi-opaque, or transparent, depending upon the use for which they are intended. For example, systems which include an optical or visual detector 28 may be fabricated, at least in part, from transparent materials to allow or facilitate that detection. Alternatively, transparent windows of glass or quartz, e.g., may be incorporated into device 10 for these types of detectors 28. Examples of preferred polymeric materials include, for example, polydimethylsiloxanes (PDMS), polyurethane, polyvinylchloride (PVC), polystyrene, polysulfone, polycarbonate, and the like.

The manufacture of channels 18 and other microscale elements, such as wells 14, 16, 22, and 30, into the surface of substrate 12 may be carried out by any number of microfabrication techniques that are well known in the art. For example, lithographic techniques may be employed in fabricating glass, quartz or silicon substrates with methods well known in the semiconductor manufacturing industries. Photolithographic masking, plasma or wet etching and other semiconductor processing techniques define microscale elements in and on substrate 12 surfaces. Alternatively, micromachining methods, such as laser drilling or ablation, air abrasion, micromilling, embossing and the like may be employed. Similarly, for polymeric substrates, well known manufacturing techniques may also be used. These techniques include injection molding techniques or stamp molding methods were large numbers of substrates may be produced using, for example, rolling stamps to produce large sheets of microscale substrates or polymer microcasting techniques wherein the substrate is polymerized within a machined mold.

Besides substrate 12, device 10 includes an additional planar element (not shown) which overlays the channeled substrate 12 to enclose and fluidly seal the various channels 18 to form conduits. The planar cover element may be attached to substrate 12 by a variety of means, including, e.g., thermal bonding, adhesives and the like. The planar cover may be provided with access ports and/or reservoirs for introducing the stock solution, base liquid and formulations into the desired wells 14, 16, 22, 24 and 30.

Alternatively, a mirror image of all or portions of substrate 12 may be formed in place of a planar element. In this manner, some or all channels 18 match up with their mifror image, producing channels 18 that may be generally symmetrical in shape. Additional details of the materials and manufacture of substrates 12 are described in U.S. Pat. No. 5,965,001 and U.S. Pat. No. 5,965,410, the complete disclosures of which are incorporated herein by reference for all purposes.

CEC capillary 26 is coupled to a detector 28 and waste well 30. As seen in FIG. 3A, two sets of wells and channels are provided. In this manner, one set of wells and channels may be used to mix and measure the control sample, and the second set of wells and channels may be used to mix and measure a test sample. A series of electrodes (not shown) are disposed within wells 14, 16, 22, 24 and 30. In this manner, electrical potentials may be applied to the electrodes to facilitate the movement of desired volumes of fluid, such as the stock solution, base liquid and formulations, through fluid channels 18 and mixing coil 20. The use of electrical potentials to control electro-osmotic forces in device 10 to promote the movement of fluids through CEC tube 26 and adjoining channels 18 is further described in previously incorporated U.S. Pat. Nos. 5,965,001and 5,965,410, and in U.S. Pat. No. 5,800,690, the complete disclosure of which is incorporated herein by reference.

In one embodiment, a stock solution is deposited into well 14, and a base liquid or formulation is deposited in one of the formulation wells 16. A desired amount of stock solution is drawn into channel 18 by applying an electrical potential between electrodes in well 14 and well 30 depicted on the right side of FIG. 3A. Similarly, a desired amount of stock solution or formulation is drawn into channel 18 by applying an electrical potential between electrodes in formulation well 16 and waste well 30 depicted near the bottom of FIG. 3A. The amount of fluid drawn from well 14 or 16 into channel 18 may be controlled by controlling the duration and voltage of the electrical potential.

The mixing of stock solution 10, having a known concentration of chemical, with the base liquid or formulation may occur by drawing the desired volumes of liquid into the mixing coil 20 using the electrical potentials. By diffusion, the control sample moves toward the CEC tube. By then applying an electrical potential between the electrodes in injection well 22 and waste well 30 depicted near the bottom of FIG. 3A, the now mixed solution is drawn into and through CEC capillary 26. By applying an electrical potential between buffer well 24 and well 30, the sample can undergo separation through the channel and then pass through the detection window (not shown, but located near or accessible by detector 28). In one particular embodiment, CEC capillary 26 comprises $C_{18}$ packed therein for use as a stationary phase of the CEC tube 26. Alternatively, $C_8$, CN, phenyl, amino, and mixed mode (ion exchange resins) and the like may be used as the stationary phase. Mixed test samples or the control sample are then measured by detector 28 for the amount of chemical contained therein. Detector 28 may be wide range of detectors, including a mass spectrometer, fluorescence, UV-Vis spectrophotometer, electrochemical and the like. Waste well 30 operates to collect the fluids and chemicals passing through CEC tube 26.

In some cases, formulations may insufficiently dissolve the chemical. As a result, precipitant may occur in fluid channel 18 and/or mixing coil 20. In this instance, it may be desirable to flush out channels 18 and coil 20 with a base liquid or other solvent after each test cycle. In another embodiment, the mixing step occurs offline from substrate 12. In this embodiment, the premixed stock solution and formulation to be tested is placed into the injection well 22, passed through CEC capillary 26, and analyzed using detector 28.

As previously noted, one advantage of the present invention is the ability to test a large number of formulations simultaneously and/or in rapid succession of one another. FIG. 3B depicts a liquid processing system 50 capable of processing a large number of formulations simultaneously. System 50 includes a substrate 12' and a series of wells, channels and CEC tubes as previously described. Further, additional sets of wells and channels are provided on substrate 12' to test the desired number of formulations. It will be appreciated by those skilled in the art that while three sets of wells and channels are shown, that a larger or smaller number of sets may be used.

FIG. 3B further depicts a controller 55 having a plurality of leads 60 coupled to the electrodes (not shown) disposed within the wells. Controller 55 operates to provide electrical potentials as well as control the duration and polarity of those potentials applied to the electrodes. In this manner, controller 55 controls the amount of liquids traveling through channels 18, 18' and the direction of travel. Controller 55 further may be configured to receive input from detector 28, 28' to produce a rank ordering of the solubility of the tested chemical within a number of formulations. It will be appreciated by those skilled in the art that while each CEC capillary 26, 26' is depicted to be connected to its own detector 28, 28', that a single detector 28 may be used for more than one, or even all CEC tubes 26, 26'.

The invention has been described in detail. However, it will be appreciated that certain changes and modifications may be made. For example, while device 10 and system 50 both depict a generally rectangular substrate 12, 12', a number of different shapes may be used. By way of example, a generally circular substrate may be used, with the detector (s) positioned near the substrate center or near the substrate periphery. Therefore, the scope and content of this invention are not limited by the foregoing description. Rather, the scope and content are to be defined by the following claims.

What is claimed is:

1. A method for evaluating the solubility of a chemical in a formulation or test media, the method comprising:

mixing a volume of a stock solution that has a known concentration of a chemical with a volume of a base liquid to form a control sample;

mixing another volume of the stock solution with a volume of a formulation to form a test sample;

passing the control sample through a capillary electrochromatography (CEC) tube to separate the chemical from the base liquid;

passing the test sample through a CEC tube to separate the chemical from the formulation;

measuring the amount of chemical passing through the CEC tubes for both the control sample and the test sample; and comparing the measured amount of chemical from the control sample with the measured amount of chemical from the test sample to determine the solubility of the chemical in the formulation relative to the base liquid.

2. A method as in claim 1, further comprising calculating the concentration of the chemical in the formation based on the comparison and the known concentration of the stock solution.

3. A method as in claim 1, further comprising mixing known volumes of the stock solution with volumes of other formulations to form multiple test samples, passing the test samples through CEC tubes, measuring the amount of chemical passing through each CEC tube, and ranking the test samples based on a comparison of the amount of chemical measured for each test sample with the amount of chemical measured from the control sample.

4. A method as in claim 1, wherein said stock solution comprises dimethyl sulfoxide (DMSO).

5. A method as in claim 1, wherein said base liquid comprises dimethyl sulfoxide (DMSO).

6. A method as in claim 1, wherein the chemical is hydrophobic.

7. A method as in claim 1, wherein the measuring step comprises counting ions with a mass spectrometer.

8. A method as in claim 1, wherein the measuring step comprises measuring a fluorescent signal emitted from the chemical.

9. A method as in claim 1, wherein the measuring step comprises measuring the amount of light absorption by the chemical.

10. A method as in claim 1, wherein the measuring step comprises measuring the amount of light scattered by the chemical.

11. A method as in claim 1, wherein the volume of base liquid and the volume of formulation are generally equal.

12. A method as in claim 1, further comprising moving the control sample and the test sample through channels formed in a substrate using electrical potentials to supply the control sample and the test sample to the CEC tubes.

13. A method as in claim 1, wherein the mixing steps comprise moving the stock solution, the base liquid and the formulation through mixing channels in a substrate using electrical potentials.

14. A method for ranking the solubility of a chemical in a plurality of formulations, the method comprising:

mixing a volume of a stock solution that has a known concentration of a chemical with a volume of a base liquid to form a control sample;

mixing other volumes of the stock solution with volumes of multiple formulations to form multiple test samples;

passing the control sample through a CEC tube to separate the chemical from the base liquid;

passing the test samples through CEC tubes to separate the chemical from the formulations;

measuring the amount of chemical passing through the CEC tubes for the control sample and the test samples; and comparing the measured amount of chemical from the control sample with the measured amount of chemical from each of the test samples to determine the solubility of the chemical in the formulations relative to the base liquid.

15. A method for ranking the solubility of a chemical in a plurality of formulations, the method comprising:

(a) providing a substrate having multiple wells and fluid delivery channels, including a stock solution well and formulation wells;

(b) placing a volume of a stock solution that has a known concentration of a chemical into the stock solution well;

(c) placing a base liquid and different formulations into the formulation wells;

(d) applying an electrical potential to mix a volume of the stock solution from the stock solution well with a volume of the base liquid from one of the formulation wells to form a control sample;

(e) applying electrical potentials to mix other volumes of the stock solution from the stock solution wells with volumes of the formulations from the formulation wells to form multiple test samples;

(f) applying electrical potentials to move the control sample and the test samples through at least some of the fluid channels and into and through CEC tubes;

(g) measuring the amount of chemical passing through the CEC tubes for the control sample and the test samples; and (h) comparing the measured amount of chemical from the control sample with the measured amount of chemical from each of the test samples to determine the solubility of the chemical in the formulations relative to the base liquid.

16. A method as in claim 15, further comprising applying said electrical potential for a desired period of time to move said volume of stock solution, said volume of base liquid and said volumes of formulations from said wells and into said fluid delivery channels.

17. A method as in claim 15, wherein applying steps (d) and (e) comprise alternating the electrical potential polarity a sufficient number of times to mix said volumes of stock solution and base liquid, and to mix said volumes of stock solution and formulations, respectively.

* * * * *